United States Patent [19]

Takaki et al.

[11] Patent Number: 4,661,620

[45] Date of Patent: Apr. 28, 1987

[54] PREPARATION PROCESS OF CINNAMATE ESTERS

[75] Inventors: Usaji Takaki, Fujisawa; Isamu Sudo; Toshio Matsuhisa, both of Yokohama; Isao Hara, Ninomiya, all of Japan

[73] Assignee: Mitsui Toatsu Chemicals, Incorporated, Tokyo, Japan

[21] Appl. No.: 780,838

[22] Filed: Sep. 27, 1985

[30] Foreign Application Priority Data

| Oct. 5, 1984 | [JP] | Japan | 59-207950 |
| Apr. 23, 1985 | [JP] | Japan | 60-85508 |
| Jul. 12, 1985 | [JP] | Japan | 60-152389 |
| Jul. 23, 1985 | [JP] | Japan | 60-161155 |
| Aug. 1, 1985 | [JP] | Japan | 60-168599 |

[51] Int. Cl.$^4$ .................. C07C 69/76; C07C 51/14
[52] U.S. Cl. ................................. 560/104; 562/406
[58] Field of Search ..................... 560/104; 562/406

[56] References Cited

U.S. PATENT DOCUMENTS 3,530,168  9/1970  Biale .................................. 560/104

FOREIGN PATENT DOCUMENTS 70836   10/1980  Japan .
15242   2/1981   Japan .
7021342 2/1982   Japan .................................. 560/104

Primary Examiner—Paul J. Killos
Attorney, Agent, or Firm—Fisher, Christen & Sabol

[57] ABSTRACT

A cinnamate ester is prepared by reacting carbon monoxide, oxygen, and its corresponding styrene compound and alcohol in the presence of a catalyst which contains, as essential components, (a) a platinum group metal or a compound thereof;
(b) a copper or iron compound; and
(c) a compound of at least one metal selected from Groups 4A, 5A, 7A, 8A(the iron group only), 1B(exclusive of copper) and 2B.

28 Claims, No Drawings

PREPARATION PROCESS OF CINNAMATE ESTERS

BACKGROUND OF THE INVENTION (1) Field of the Invention

This invention relates to a process for preparing a cinnamate ester by reacting carbon monoxide, oxygen, and its corresponding styrene compound and alcohol.

(2) Description of the Prior Art

Cinnamate esters have found wide-spread commercial utility as perfumes, fragrant materials, flavors and the like and raw materials therefor owing to their inherent aroma. They are also important as raw materials for agricultural chemicals and photosensitive resins.

Cinnamic acid has conventionally been produced on small scales by using benzaldehyde and derivatives of acetic acid as principal raw materials. This process is however not preferred from the industrial viewpoint since it requires such costly raw materials.

As processes permitting use of more economical raw materials, it has also been proposed to prepare a cinnamate ester by reacting carbon monoxide, oxygen and its corresponding styrene compound and alcohol in the presence of a catalyst (see, for example, Japanese Patent Laid-Open Nos. 15242/1981 and 70836/1982).

In these processes, the activities of the catalysts are however still low and their reaction results are not fully satisfactory. For these reasons, they have not yet been practiced on any industrial scales.

SUMMARY OF THE INVENTION

The first object of this invention is to provide a process for advantageously preparing a cinnamate ester by reacting carbon monoxide, oxygen, and its corresponding styrene compound and alcohol.

The second object of this invention is to provide a catalyst system (which may hereinafter be called "catalyst" for the sake of simplification) which allows to conduct the above reaction at a mild temperature, at a high reaction velocity and with good reaction results.

The third object of this invention is to provide a catalyst in which the catalytic efficiency of a platinum group metal, a principal component of the catalyst, has been enhanced to assure high activities.

The fourth object of this invention is to provide a catalyst which permits use of a low total reaction pressure and allows the reaction to proceed at low partial pressures of carbon monoxide and oxygen.

The fifth object of this invention is to provide an industrial preparation process which permits addition of carbon dioxide to the reaction system for improved reaction results and facilitates the reutilization of spent gas.

Other objects will become apparent from the ensuing description of this invention.

DETAILED DESCRIPTION OF THE PREFERRED EMBODIMENTS

The above objects of the present invention have been achieved by the following process of this invention:

A process for preparing a cinnamate ester by the reaction of carbon monoxide, oxygen, and its corresponding styrene compound and alcohol, which comprises conducting the reaction in the presence of a catalyst containing, as essential components, (a) a platinum group metal or a compound thereof;

(b) a copper or iron compound; and (c) a compound of at least one metal selected from Groups 4A, 5A, 7A, 8A(the iron group only), 1B(exclusive of copper) and 2B of the periodic table.

As preferred embodiments of the process of this invention, may be mentioned to have a halogen compound exist in the reaction and to have carbon dioxide exist in the feed gas.

The above-described process of this invention can bring about inter alia the following advantageous effects:

(1) The reaction can be carried out at a relatively mild reaction temperature.

(2) A high reaction velocity can be achieved.

(3) Good reaction results are assured. Namely, it is possible to improve the conversion of the styrene compound, the selectivity toward the intended cinnamate ester and the yield of the intended cinnamate ester.

(4) The catalyst enjoys high activities, whereby a high reaction velocity is assured. Namely, the platinum group metal has a high turnover number (i.e., the mole number of the cinnamate ester prepared per gram atom of the platinum group metal, the first component of the catalyst) and a high turnover frequency (i.e., the mole number of the cinnamate ester prepared per gram atom of the platinum group metal, the first component of the catalyst, and per hour of the reaction time). The process of this invention thus requires such an expensive noble metal in a smaller amount, leading to an economical advantage.

(5) Feed gases such as carbon monoxide and oxygen can be used at low partial pressures. They can thus be diluted to significant degrees with an inert gas. It is thus possible to avoid the explosion hazard.

(6) The process of this invention permits use of a low total pressure. This is certainly economical from the viewpoint of the reaction apparatus. It is thus possible to use a glass-lined reactor.

(7) Since the catalytic activities are not deleteriously affected by water which is to be formed by the reaction, it is unnecessary to add any desiccant to the reaction system.

(8) Incorporation of carbon dioxide in the reaction system leads to more preferable results. It is not absolutely necessary to separate and remove carbon dioxide from spent gas by a special method when spent gas is repeatedly used. This feature is extremely advantageous from the industrial viewpoint.

As has been mentioned above, a variety of advantageous effects can be obtained from the practice of the process of this invention. Therefore, this invention provides an industrially-advantageous process for the preparation of cinnamate esters.

As specific styrene compounds useful in the practice of the process of this invention, may be mentioned styrene; alkyl derivatives of styrene, such as $\alpha$-methylstyrene, $\beta$-methylstyrene, $\alpha$-ethylstyrene, $\beta$-ethylstyrene, o-methylstyrene, m-methylstyrene, p-methylstyrene, m-ethylstyrene, p-ethylstyrene, p-tertbutylstyrene and $\beta$-methyl-p-isopropylstyrene; and other styrene derivatives having, on their aromatic rings, substituent groups which do not impair the intended reactions, such as p-chlorostyrene, p-methoxystyrene and 3,4-dimethoxystyrene.

As exemplary alcohols, may be mentioned methanol, ethanol, propanol, butanol, pentanol, octanol, cyclopentanol, cyclohexanol, phenol, benzylalcohol, ethylene glycol, polyethylene glycol, propylene glycol, etc.

These alcohols may contain substitutents which do not impair the respective reactions, such as halogen, alkoxy groups and the like. These alcohols may each be used in an amount of 0.5–100 parts by mole per mole of the styrene compound. They may be used not only as reaction raw materials but also as reaction solvents.

In the reaction according to the process of this invention, the alcohol as a raw material may practically be used as a solvent. Other solvents may however be used so long as they do not impair the reaction. Illustrative of such other solvents are ethers such as diethyl ether, dipropyl ether, methyl ethyl ether, phenyl ethyl ether, diphenyl ether, tetrahydrofuran, dioxane, ethylene glycol diethyl ether and tetraethylene glycol dimethyl ether, ketones such as acetone, methyl ethyl ketone and acetophenone, esters such as methyl acetate, ethyl acetate and methyl propionate, aromatic hydrocarbons such as benzene, toluene, p-xylene, ethylbenzene, chlorobenzene and dichlorobenzene and their substituted compounds, aliphatic and alicyclic hydrocarbons such as n-hexane, n-pentane and cyclohexane, carbonates such as propylene carbonate and dimethyl carbonate, nitriles such as acetonitrile and benzonitrile, aromatic nitro compounds such as nitrobenzene, amide compounds such as dimethylformamide, sulfone compounds such as sulfolane, etc.

The catalyst useful in the practice of the process of this invention contains, as essential components, a platinum group metal or a compound thereof as a first component;

a copper or iron compound as a second component; and a compound of at least one metal selected from Groups 4A, 5A, 7A, 8A(the iron group only), 1B(exclusive of copper) and 2B of the periodic table published by International Union of Pure and Applied Chemistry, as a third component.

As the platinum group metal or its compound as the first component of the catalyst, may be mentioned a metal such as ruthenium, rhodium, palladium, osmium, iridium or platinum, or its halide, nitrate, sulfate, phosphate, organic acid salt, complex compound or oxide. Of these, metallic palladium or its compound is preferred. As examples of metallic palladium and its compound, may be mentioned palladium black, metallic palladium supported on a carriers such as activated carbon, graphite, asbestos, alumina, silica, silica alumina, magnesia, zeolite, Molecular Sieves, or an ion exchange resins, null-valent palladium complexes such as dibenzylideneacetone complex and tetrakis(triphenylphosphine)palladium, and divalent palladium compounds such as the palladium salts of inorganic acids, e.g., palladium chloride and palladium nitrate, the palladium salts of organic acids, e.g., palladium acetate and palladium benzoate, and palladium complexes, e.g., bis(acetylacetonate)palladium, cyclooctadiene dichloropalladium, bis(benzonitrile)palladium chloride complex, bis(pyridine)palladium chloride complex and palladium chloride ammine complex.

These platinum group metals and their compounds may be used either singly or in combination.

These platinum group metals or their compounds may each be used in an amount of 0.1 gram atom or less, or preferably $5 \times 10^{-6} - 1 \times 10^{-2}$ gram atom as calculated in terms of the platinum metal atom, per mole of the styrene compound as a raw material.

As the copper or iron compound as the second component of the catalyst, may be mentioned a halide of copper or iron, the nitrate, sulfate, phosphate or carbonate of copper or iron, the copper or iron salt of an organic acid, a complex compound of copper or iron, or the like. Illustrative of the copper compound may be copper halides such as copper chloride and copper bromide, the copper salts of inorganic acids such as copper carbonate and copper nitrate, the copper salts of organic acids such as copper acetate, copper propionate, copper stearate, copper cinnamate, copper benzoate and copper toluenesulfonate, and copper complex compounds such as copper acetylacetonate and copper benzoylacetonate. As iron compounds, iron compounds similar to the above-described copper compounds may be mentioned.

The preferable second component of the catalyst may be a copper compound, more preferably, the copper salt of an organic acid such as copper acetate, copper propionate, copper stearate, copper cinnamate, copper benzoate or copper toluenesulfonate, or a copper complex compound such as copper acetylacetonate or copper benzoylacetonate.

These copper and iron compounds may be used either singly or in combination. It is preferable that these compounds are dissolved in liquid reaction mixtures. No problems or inconvenience are however encountered even if they remain partly in their undissolved forms. These compounds are caused to exist in liquid reaction mixtures, each, at such a concentration of 0.004–0.4 gram atom per liter as calculated in terms of metallic copper or iron atoms.

Illustrative of the compound of at least one metal selected from Groups 4A, 5A, 7A, 8A(the iron group only), 1B(exclusive of copper) and 2B of the periodic table published by International Union of Pure and Applied Chemistry which compound is the third component of the catalyst, may specifically be the following compounds of Group 4A metals (titanium, zirconium and hafnium), Group 5A metals (vanadium, niobium and tantalum), Group 7A metals (manganese, technetium and rhenium), Group 8A(the iron group only) (iron, cobalt and nickel) Group 1B metals (silver and gold) and Group 2B metals (zinc, cadmium and mercury); inorganic compounds such as the oxide, hydroxides, halides and carbonates, etc.; or salts of organic acids each of which contains one or two acidic groups, such as acetic acid, propionic acid, stearic acid, succinic acid, phenylacetic acid, cinnamic acid, benzoic acid, phthalic acid and toluenesulfonic acid, etc.; or complex compounds such as acetylacetonate complexes, cyclopentadienyl complexes and carbonyl complexes; etc. Compounds of at least one metal selected from Groups 5A, 7A, 8A(the iron group only) and 2B are preferred, with vanadium, manganese, cobalt, nickel and zinc compounds being more preferred.

When an iron compound is used as the second component of the catalyst, a compound of a metal other than iron is used as the third component of the catalyst.

Two or more of these compounds may be used in combination. It is preferred that these compounds are dissolved in liquid reaction mixtures. No problems or inconvenience are however encountered even if they are partly in their undissolved forms. These compounds may each be used, as the third component of the catalyst, in such an amount that the gram atom ratio of the contained metallic atom to copper or iron atoms contained in the liquid reaction mixture is 0.01–50 with 0.05–10 being preferred.

No problems or inconvenience will arise even when instead of using the above-described compounds as the first, second and third components of the catalyst, combinations of compounds capable of yielding such compounds in the reaction system are used.

In the process of this invention, an additional inclusion of a halogen compound in the catalyst system composed of the aforementioned first, second and third components can improve the reaction results and catalytic activities further and can also employ milder reaction conditions. This additional halogen compound may be the first, second and/or third components of the catalyst. Alternatively, a further halogen compound may also be used as the additional halogen compound.

Illustrative of preferable halogen compounds may be halogen molecules such as chlorine, bromine and iodine and their solutions; hydrogen halides such as hydrogen chloride, hydrogen bromide and hydrogen iodide and their solutions; organohalogen compounds capable of yielding halogen ions readily, including tertiary alkyl halides such as tertiary butyl chloride and tertiary butyl bromide and acid halides such as acetyl chloride and benzoyl chloride; halogen-containing carbonic acid derivatives such as phosgene and methyl chloroformate; phosphorus halides such as phosphorus trichloride, phosphorus pentachloride, phosphorus tribromide and phosphorus pentabromide; phosphorus oxyhalides such as phosphoryl chloride and phosphoryl bromide; thionyl halides such as thionyl chloride and thionyl bromide; tellurium halides such as tellurium tetrachloride and tellurium tetrabromide; and the halides and oxyhalides of Group 4A metals such as titanium and zirconium, Group 5A metals such as vanadium and tantalum, Group 6A metals such as chromium and molybdenum, Group 7A metals such as manganese, Group 8A metals such as iron, cobalt, nickel and palladium, Group 1B metals such as copper and silver, Group 2B metals such as zinc and cadmium, Group 4B metals such as germanium and tin and Group 5B metals such as antimony and bismuth, in each of which the number of halogen atoms or oxyhalogen moieties corresponds to the valence of the associated metal. Of these halogen compounds, chlorine, hydrogen chloride, hydrogen bromide, phosphorus pentachloride, phosphoryl chloride, vanadium oxytrichloride, chromium trichloride, manganese chloride, iron chloride, iron bromide, copper chloride, copper bromide, zinc chloride, tin chloride, bismuth chloride and the like are preferred, with the chloride compounds being more preferred. These halogen compounds may be used either singly or in combination.

The halogen compound may be used at a concentration of 0.004–0.8 gram atom as calculated in terms of halogen atoms per liter of the corresponding liquid reaction mixture, with 0.008–0.6 gram atom being preferred.

When a halogen compound is used as mentioned above, more preferable results may be obtained by conducting a reaction in such a way that in the copper compound employed as the second component, the concentration of copper atoms in the corresponding liquid reaction mixture is controlled at 0.004–0.4 gram atom per liter and the ratio by gram atom of halogen atoms to the copper atoms is adjusted to a value smaller than 2, preferably, 0.02–1.99. In order to achieve such a ratio of halogen atoms to copper atoms, it is necessary in most cases to use separate compounds as the copper-source compound and halogen-source compound or to employ a separate compound as at least part of the copper-source compound or halogen-source compound.

In the process of this invention, carbon monoxide and oxygen are used as raw materials. In order to maintain their mixture out of inflammability limit, it is preferred to dilute them with an inert gas such as nitrogen or argon. Air may be used as an oxygen source. The partial pressure of carbon monoxide is below 50 atms (absolute atmospheric pressure; all designations of "atm" will hereinafter mean atmospheric ressure as absolute pressure), with the range of 0.005–40 atms being preferred. The partial pressure of oxygen is also below 50 atms with the range of 0.002–30 atms being preferred.

Still better reaction results and catalytic activities can be obtained when carbon dioxide is intentionally caused to exist in the reaction system upon conducting the process of this invention. The present inventors are not aware of any prior art in which, in a reaction system for preparing a cinnamate ester by the reaction of carbon monoxide, oxygen and its corresponding styrene compound and alcohol, the reaction was carried out in the presence of intentionally-added carbon dioxide, resulting in the development of such effects as mentioned above.

When carbon dioxide is used, its partial pressure is below 500 atms, or preferably 0.1–300 atms. It is however preferred to control the partial pressure of carbon dioxide above 10% (by pressure) based on the total pressure of the reaction, in other words, to maintain the concentration of carbon dioxide in the reaction gas mixture above 10% by volume, with the range of 10%–98% being more preferred. If the concentration of carbon dioxide is lower than 10%, the effects of carbon dioxide cannot be brought about. Any concentrations of carbon dioxide higher than 98% lead to lowered concentrations of carbon monoxide and oxygen, thereby making the reaction velocity slower. Most preferably, the concentration of carbon dioxide may be within the range of 15–95%.

Carbon monoxide and oxygen, and carbon dioxide and inert gas if used may be charged together in their respective required amounts to a reactor. Alternatively, desired gases may be additionally fed either continuously or intermittently or their mixed gas may be caused to flow either continuously or intermittently. Of these feeding methods, the additional feeding or the continuous or intermittent flow is more preferred.

The feed gas mixture, which is to be provided for the reaction, may be prepared freshly whenever the reaction is carried out. Alternatively, a residual gas still remaining after once used in the reaction or a spent gas in the flowing method may be repeatedly used after the concentrations of the individual gas components have been adjusted as needed. In the reaction of the present invention, carbon dioxide may be formed from carbon monoxide and oxygen as a result of a side reaction. Since the presence of carbon dioxide is rather preferred in the process of this invention, it is not always necessary to separate and remove resulting carbon dioxide by a special method when residual gas or spent gas is repeatedly used.

Carbon dioxide in the residual or spent gas may be used for the entire or partial portion of carbon dioxide to be caused to exist in the reaction.

The process of this invention may be practiced as any one of batch reaction, semi-batch reaction and continuous flow reaction.

In the process of this invention, the total pressure of the reaction is generally below 500 atoms with 1-300 atoms being preferred, although it may certainly vary depending on the partial pressures of carbon monoxide, oxygen and carbon dioxide or the partial pressure of the inert gas. The reaction temperature may range from room temperature to 200° C. with 40° C.-160° C. being preferred. The reaction time varies depending on reaction conditions, but may generally range from 0.01-24 hours with 0.05-10 hours being preferred.

After completion of the reaction, the intended cinnamate ester can be isolated from the liquid reaction mixture by a routine technique for isolation such as distillation or extraction.

[Examples]

The present invention will hereinafter be described in more detail by the following Examples and Comparative Examples.

EXAMPLE 1

In a 200-ml autoclave, wherein the inside walls of the autoclave and its accessories were protected with glass at areas where they were brought into contact with liquid reaction mixtures, were charged 50 mg (0.28 millimole) of palladium chloride, 700 mg (5.2 millimoles) of cupric chloride, 2.8 g (12.7 millimoles) of zinc acetate dihydrate, 10.4 g (100 millimoles) of styrene and 32 g (1.00 mole) of methanol. After feeding under pressure 22.5 kg/cm$^2$G of carbon monoxide, 188 kg/cm$^2$G of a mixed gas of oxygen and nitrogen in which the oxygen content had been diluted to 6 vol.% was fed under pressure to achieve an oxygen partial pressure of 11.3 kg/cm$^2$G. With stirring, the contents were heated to 120°-130° C. at which they were held for 30 minutes. After completion of the reaction, the autoclave was cooled and its pressure was released. The resultant liquid reaction mixture was taken out of the autoclave, then filtrated. The composition of the filtrate was analyzed by high-speed liquid chromatography. The filtrate contained 38.8 millimoles of styrene, 52.2 millimoles of methyl cinnamate and 3.7 millimoles of dimethyl phenylsuccinate. The conversion of styrene was 61.2%. The yields of methyl cinnamte and dimethyl phenyl succinate were 85.3% and 6.0% respectively, both on the consumed styrene.

The number of moles of the cinnamate ester formed per gram atom of the platinum group metal contained as the first component in the above-used catalyst (moles/gram atom; will hereinafter be called "turnover number") was 186, and its turnover frequency per hour [mole/(gram atom·hr.)] was 373.

EXAMPLE 2

The procedures of Example 1 were exactly repeated except that 100 mg of palladium chloride was charged and the reaction was carried out at 100°-120° C. for 10 minutes. The conversion of styrene was 63.1%, while the yield of methyl cinnamate was 87.2% based on the consumed styrene. The turnover frequency of palladium was 590.

EXAMPLE 3

Raw materials were charged in the same manner as in Example 1 except that a 200-ml TEFLON-lined autoclave equipped with a water-cooled condenser was used and 48 g of methanol was used. A mixed gas of carbon monoxide, oxygen and nitrogen in a volume ratio of 12:6:94 was adjusted in pressure to maintain a total pressure of 150 kg/cm$^2$G during the reaction and was then caused to flow through the autoclave at a velocity of 500 ml/min. (under standard conditions) at the outlet of the autoclave. While feeding the mixed gas, the reaction gas was discharged through the condenser. When reacted at 100° C. for 30 minutes, the conversion of styrene was 63.8% and the yield of methyl cinnamate reached 82.6% based on the consumed styrene. The turnover frequency was 403.

EXAMPLE 4

In a 50-ml autoclave with a TEFLON cup inserted therein, were charged 11.0 mg (0.062 millimole) of palladium chloride, 73.4 mg (0.55 millimole) of cupric chloride, 217 mg (0.75 millimole)of manganese(II) acetylacetonate dihydrate, 1.15 g (11.0 millimoles) of styrene and 10.0 g (312 millimoles) of methanol. Thereafter, 13.5 kg/cm$^2$G of carbon monoxide was charged under pressure and 112 kg/cm$^2$G of a mixed gas of oxygen and nitrogen, in which the content of oxygen was 6 vol.%, was fed under pressure to achieve an oxygen partial pressure of 6.7 kg/cm$^2$G. The contents were reacted at 100° C. for 30 minutes. As a result of a post treatment and analysis in the same manner as in Example 1, the conversion of styrene was 73% while the yield of methyl cinnamate was 65% based on the consumed styrene. The turnover frequency of palladium was 168.

EXAMPLES 5-19 & COMPARATIVE EXAMPLES 1 and 2

Reactions were carried out in exactly the same manner as in Example 4, except that in lieu of manganese(II) acetylacetonate dihydrate employed in Example 4, the compounds given in Table 1 were used in their respective amounts. Results are also shown in Table 1.

TABLE 1

| Ex. & Comp. Ex. | Catalyst component (c) | | Conversion of styrene (%) | Yield of methyl cinnamate based on consumed styrene (%) | Turnover frequency mole/(gram atom · hr) |
| --- | --- | --- | --- | --- | --- |
| | Compound | Used amount (millimole) | | | |
| Ex. 5 | titanyl (II) acetylacetonate TiO(acac)$_2$* | 0.56 | 70 | 57 | 142 |
| Ex. 6 | zirconium (IV) acetylacetonate Zr(acac)$_4$ | 0.28 | 84 | 72 | 215 |
| Ex. 7 | manganese benzoate tetrahydrate Mn(C$_6$H$_5$COO)$_2$.4H$_2$O | 0.56 | 84 | 50 | 149 |
| Ex. 8 | iron (III) acetylacetonate | 0.37 | 87 | 68 | 210 |

TABLE 1-continued

| Ex. & Comp. Ex. | Catalyst component (c) Compound | Used amount (millimole) | Conversion of styrene (%) | Yield of methyl cinnamate based on consumed styrene (%) | Turnover frequency mole/(gram atom · hr) |
|---|---|---|---|---|---|
| Ex. 9 | Fe(acac)$_3$ ferrocene | 0.56 | 61 | 60 | 130 |
| Ex. 10 | cobalt acetate tetrahydrate Co(CH$_3$COO)$_2$.4H$_2$O | 0.56 | 91 | 49 | 158 |
| Ex. 11 | nickel acetate tetrahydrate Ni(CH$_3$COO)$_2$.4H$_2$O | 0.56 | 70 | 66 | 164 |
| Ex. 12 | nickel (II) acetylacetonate dihydrate Ni(acac)$_2$.2H$_2$O | 0.56 | 75 | 62 | 165 |
| Ex. 13 | silver acetate CH$_3$COOAg | 1.12 | 73 | 73 | 189 |
| Ex. 14 | zinc stearate (CH$_3$(CH$_2$)$_{16}$COO)$_2$Zn | 0.56 | 67 | 80 | 190 |
| Ex. 15 | zinc oxide ZnO | 0.56 | 90 | 52 | 166 |
| Ex. 16 | zinc hydroxide Zn(OH)$_2$ | 0.56 | 69 | 53 | 130 |
| Ex. 17 | basic zinc carbonate 2Zn(CO)$_3$.3Zn(OH)$_2$.H$_2$O | 0.14 | 95 | 75 | 253 |
| Ex. 18 | zinc chloride + acetic acid ZnCl$_2$ + CH$_3$COOH | ZnCl$_2$ 0.56 CH$_3$COOH 2.33 | 95 | 45 | 152 |
| Ex. 19 | cadmium acetate dihydrate Cd(CH$_3$COO)$_2$.2H$_2$O | 0.56 | 66 | 61 | 143 |
| Comp. Ex. 1 | none | 0 | 65 | 2 | 4.6 |
| Comp. Ex. 2 | potassium acetate CH$_3$COOK | 1.12 | 39 | 49 | 68 |

*"acac" stands for an acetylacetonate group.

COMPARATIVE EXAMPLE 3

The procedures of Example 10 were exactly repeated except that cupric chloride was not used. The conversion of styrene was 1.1% and methyl cinnamate was not formed at all.

EXAMPLE 20

A reaction was conducted in exactly the same manner as in Example 4 except that 5% Pd/C (catalyst composed of 5 wt. % of palladium carried on activated carbon) was used in an amount equivalent to 0.062 milligram atom in terms of palladium instead of palladium chloride and 0.56 millimole of manganese acetate tetrahydrate was used in place of manganese(II) acetylacetonate dihydrate. The conversion of styrene was 70% while the yield of methyl cinnamate was 63% based on the consumed styrene.

EXAMPLE 21

The procedures of Example 1 were followed in exactly same manner except that the amount of palladium chloride was changed to 100 mg (0.56 millimole), 3.26 g (20 millimoles) of ferric chloride was used in place of cupric chloride, and the reaction time was reduced to 17 minutes. The conversion of styrene was 51%, while the yield of methyl cinnamate was 45% based on the consumed styrene.

EXAMPLES 22 & 23

Reactions were respectively carried out in exactly the same manner as in Example 4 except that ethanol was used instead of methanol in the same amount as methanol, 0.56 millimole of zinc acetate dihydrate was used in place of manganese(II) acetylacetonate dihydrate (Example 22), and α-methylstyrene was used in lieu of styrene (Example 23). Based on the consumed styrene and styrene compound, the yields of the resultant cinnamate esters were respectively 82% (Example 22) and 66% (Example 23).

EXAMPLE 24

The procedures of Example 3 were exactly repeated except that the mixed gas was changed to another mixed gas of carbon monoxide, oxygen and carbon dioxide having a volume ratio of 12:6:94 and the total pressure of the reaction was changed to 51 kg/cm$^2$G. The conversion of styrene was 73.8%, while the yield of methyl cinnamate was 89.1% based on the consumed styrene. The turnover frequency was 470.

EXAMPLE 25

Added to a glass-made cylindrical vessel were 7.1 mg (0.040 millimole) of palladium chloride, 1.20 g (6.01 millimoles) of cupric acetate monohydrate and 3.82 g (15.6 millimoles) of manganese(II) acetate tetrahydrate. By using 10.5 ml of a methanol solution of hydrogen chloride (concentration: 1.25N), the amount of hydrogen chloride was adjusted to 13.1 millimoles. 26.04 g (250.0 millimoles) of styrene was then provided, to which methanol was added to increase the total volume to 125 ml. The concentrations of copper atoms and chlorine atoms were respectively 0.048 and 0.105 gram atom per liter of the liquid reaction mixture. The glass vessel was then inserted in a 500-ml autoclave. The stirring blades of the autoclave were made of glass and its temperature measurement tube was also protected with glass. While maintaining the total pressure of the autoclave at 10 atms and causing a mixed gas of carbon monoxide, oxygen and carbon dioxide having a partial pressure ratio of 8.3:5.4:86.3 to pass through the autoclave at a flow velocity of 1.2 liters per minute (under standard conditions) at the outlet of the autoclave, the contents were continuously stirred so that they were reacted at 100° C. for 3 hours. During the reaction, the outlet gas was discharged through a water-cooled reflux condenser. After completion of the reaction, the liquid reaction mixture was cooled and taken out of the autoclave. It was thereafter analyzed by high-speed liquid chromatography. As a result, it was found that the liquid reaction mixture contained 38.0 millimoles of styrene, 189.5 millimoles of methyl cinnamate and 8.5 millimoles of dimethyl phenylsuccinate. The conversion of styrene was 84.8%, the selectivity toward methyl cinnamate (its yield based on the consumed styrene) was 89.4%, and the yield of methyl cinnamte (based on the charged styrene) was 75.8%. The turnover number of palladium as the first component of the catalyst was 4740 (moles/gram atom) and its turnover frequency was 1580 [moles/(gram atom·hr)].

EXAMPLE 26

Placed in a glass-made cylindrical vessel were 11.23 mg (0.050 millimole) of palladium acetate, 2.50 g (12.5 millimoles) of cupric acetate monohydrate and 3.82 g (15.6 millimoles) of manganese(II) acetate tetrahydrate. After adding a small amount of methanol to the vessel, 26.04 g (250.0 millimoles) of styrene was also charged in the vessel. A methanol solution with hydrogen chloride absorbed therein, the concentration of which solution had been measured (about 0.5–2N) right before its addition, was then added in such an amount that hydrogen chloride reached 6.25 millimoles. Thereafter, methanol was added to increase the total volume to 125 ml.

The concentration of copper atoms was 0.10 gram atom per liter of the liquid reaction mixture, while the gram atom ratio of chlorine atoms to the copper atoms was 0.50. The glass vessel was then inserted in a 500-ml autoclave. The stirring blades of the autoclave were made of glass and its temperature measurement tube was also protected with glass.

While maintaining the total pressure of the autoclave at 50 kg/cm$^2$G and causing a mixed gas of carbon monoxide, oxygen and nitrogen having a partial pressure ratio of 10:5:85 to pass through the autoclave at a flow velocity of 1.2 liters per minute (under standard conditions) at the outlet of the autoclave, the contents were continuously stirred so that they were reacted at 100° C. for 3 hours. During the reaction, the outlet gas was discharged through a water-cooled reflux condenser. After the reaction, the liquid reaction mixture was cooled and the pressure of the autoclave was released. The liquid reaction mixture was then taken out of the autoclave and was then analyzed by high-speed liquid chromatography. As a result, it was found that the liquid reaction mixture contained 12.25 millimoles of styrene, 217.8 millimoles of methyl cinnamate and 8.25 millimoles of byproduced dimethyl phenylsuccinate. The conversion of styrene was 95.1%, the selectivity toward methyl cinnamate (its yield based on the consumed styrene) was 91.6%, and the yield of methyl cinnamte (based on the charged styrene) was 87.1%. The selectivity toward dimethyl phenylsuccinate was 3.5% and its yield was 3.3%. The number of moles of the cinnamate ester produced per gram atom of palladium, namely, the turnover number was 4360.

EXAMPLE 27

Provided were 8.87 mg (0.050 millimole) of palladium chloride, 2.19 g (10.97 millimoles) of cupric acetate monohydrate, 0.206 g (1.53 millimoles) of cupric chloride and 3.82 g (15.6 millimoles) of manganese(II) acetate tetrahydrate. After adding a small amount of methanol, 26.04 g (250.0 millimoles) of styrene was added, followed by a further addition of methanol to make the total volume be 125 ml. The concentration of copper atoms per liter of the liquid reaction mixture was 0.10 gram atom, while the gram atom ratio of all chlorine atoms to all the copper atoms was 0.25. They were reacted in the same manner as in Example 26. The conversion of styrene was 94.3%, while the selectivity toward methyl cinnamate and its yield were 92.8% and 87.5% respectively. The turnover number of palladium was 4380.

COMPARATIVE EXAMPLES 4 AND 5 & EXAMPLES 28, 29 AND 30

Reactions were carried out in exactly the same manner as in Example 27 except that cupric acetate monohydrate and cupric chloride were used in their corresponding amounts shown in Table 2. In each of the Comparative Examples and Examples, the ratio of chlorine atoms to copper atoms was 1.0. Results are given in Table 2.

TABLE 2

| | Cu(OAc)$_2$.H$_2$O* (millimole) | CuCl$_2$ (millimole) | Cu concentration (gram atom/liter) | Yield of methyl cinnamate (%) | Turnover number (mole/gram atom) |
|---|---|---|---|---|---|
| Comp. Ex. 4 | 0.20 | 0.11 | 0.0024 | 4.7 | 230 |
| Ex. 28 | 1.62 | 1.51 | 0.025 | 70.4 | 3520 |
| Ex. 29 | 6.37 | 6.16 | 0.10 | 80.3 | 4020 |
| Ex. 30 | 15.7 | 15.6 | 0.25 | 65.3 | 3270 |
| Comp. Ex. 5 | 31.3 | 31.2 | 0.50 | 40.2 | 2010 |

*"OAc" stands for an acetate group.

EXAMPLES 31–35

Reactions were carried out in exactly the same manner as in Example 27 except that the amounts of cupric acetate monohydrate and cupric chloride and the type of the palladium compound were changed as shown in Table 3. In each of the Examples, the concentration of copper atoms per liter of the liquid reaction mixture was 0.1 gram atom. Results are given in Table 3, along with results of the above-described Examples 27 and 29.

TABLE 3

|  | Ex. 31 | Ex. 27 | Ex. 32 | Ex. 33 | Ex. 29 | Ex. 34 | Ex. 35 |
|---|---|---|---|---|---|---|---|
| Palladium compound | $PdCl_2$ | $PdCl_2$ | $Pd(OAc)_2$ | $PdCl_2$ | $PdCl_2$ | $PdCl_2$ | $Pd(OAc)_2$ |
| $Cu(OAc)_2.H_2O$* (millimole) | 12.1 | 11.0 | 10.9 | 9.40 | 6.37 | 3.20 | — |
| $CuCl_2$ (millimole) | 0.39 | 1.53 | 1.58 | 3.12 | 6.16 | 9.32 | 12.5 |
| Cl/Cu ratio by gram atom | 0.07 | 0.25 | 0.25 | 0.51 | 0.99 | 1.5 | 2 |
| Conversion of styrene (%) | 80.4 | 94.3 | 95.0 | 89.9 | 96.1 | 91.3 | 96.5 |
| Selectivity toward methyl cinnamate (%) | 82.6 | 92.8 | 91.4 | 93.7 | 83.6 | 83.3 | 48.4 |
| Yield of methyl cinnamate (%) | 66.4 | 87.5 | 86.8 | 84.2 | 80.3 | 76.1 | 46.7 |
| Turnover number (mole/gram atom) | 3320 | 4380 | 4340 | 4210 | 4020 | 3810 | 2340 |

*"OAc" stands for an acetate group.

EXAMPLE 36

A reaction was carried out in exactly the same manner as in Example 27 except that 180 mg (0.085 milligram atoms as palladium) of 5% Pd/C (a catalyst composed of 5 wt. % of palladium carried on activated carbon) was used in lieu of palladium chloride and the amounts of cupric acetate monohydrate and cupric chloride were changed to 1.89 g (9.47 millimoles) and 419 mg (3.12 millimoles) respectively. The concentration of copper atoms per liter of the liquid reaction mixture was 0.1 gram atom. The ratio of chlorine atoms to the copper atoms was 0.50.

The conversion of styrene was 86.4%, while the selectivity toward methyl cinnamate and its yield were 79.6% and 68.8% respectively.

EXAMPLE 37

The procedures of Example 27 were exactly followed except that p-chlorostyrene and ethanol were used respectively instead of styrene and methanol and the amount of palladium chloride was changed to 0.1 millimole. Ethyl 4-chlorocinnamate was obtained with a yield of 60.2%.

EXAMPLE 38

A reaction was carried out in exactly the same manner as in Example 26 except that the amount of palladium acetate was changed to 9.0 mg (0.04 millimole) and a solution obtained by causing methanol to absorb chlorine gas in place of hydrogen chloride gas was used to adjust the amount of chlorine atoms to 6.26 milligram atom. The concentration of copper atoms per liter of the liquid reaction mixture was 0.10 gram atom. The gram atom ratio of the chlorine atoms to the copper atoms was 0.50.

The conversion of styrene was 94.8%, while the selectivity toward methyl cinnamate and its yield were 82.3% and 78.0% respectively. The turnover number of palladium was 4880.

EXAMPLES 39–43

Reactions were carried out in exactly the same manner as in Example 27 except that the palladium compounds shown in Table 4 were each used in an amount of 0.04 millimole and the amounts of the other catalyst components and the type and amount of the halogen compound were changed as given in Table 4. Results are shown in Table 4, along with results of Example 38.

TABLE 4

|  | Ex. 38 | Ex. 39 | Ex. 40 | Ex. 41 | Ex. 42 | Ex. 43 |
|---|---|---|---|---|---|---|
| Palladium compound | $Pd(OAc)_2$* | $PdCl_2$ | $PdCl_2$ | $Pd(OAc)_2$ | $PdCl_2$ | $PdCl_2$ |
| Components (millimoles) |  |  |  |  |  |  |
| 2nd component of catalyst | $Cu(OAc)_2.H_2O$ 12.5 | $Cu(Phcoo)_2.2H_2O$ 12.5 | $Cu(OAc)_2.H_2O$ 25.1 | $Cu(OAc)_2.H_2O$ 12.5 | $Cu(OAc)_2.H_2O$ 12.5 | Copper stearate 12.5 |
| Halogen compound | $Cl_2$ 3.13 | $FeCl_3$ 2.05 | $VOCl_3$ 4.17 | $ZnCl_2$ 6.22 | $POCl_3$ 2.05 | $CuCl_2$ 1.53   $MnCl_2$ 1.53 |
| 3rd component of catalyst | $Mn(OAc)_2.4H_2O$ 15.6 | $Mn(acac)_2.2H_2O$** 15.6 | $Zn(OAc)_2.H_2O$ 14.8 |  | $Mn(Phcoo)_2.4H_2O$ 15.2 | $Mn(OAc)_2.4H_2O$ 13.6 |
| Cu concentration (gram atom/liter) | 0.10 | 0.10 | 0.20 | 0.10 | 0.10 | 0.11 |
| Cl/Cu ratio by gram atom | 0.50 | 0.50 | 0.50 | 1.00 | 0.50 | 0.44 |
| Yield of methyl cinnamate (%) | 78.1 | 66.3 | 77.5 | 62.0 | 76.3 | 58.8 |
| Turnover number | 4880 | 4140 | 4840 | 3880 | 4770 | 3680 |

TABLE 4-continued

| | Ex. 38 | Ex. 39 | Ex. 40 | Ex. 41 | Ex. 42 | Ex. 43 |
|---|---|---|---|---|---|---|
| (mole/gram atom) | | | | | | |

*"OAc" stands for an acetate group.
**"acac" stands for an acetylacetonate group.

EXAMPLE 44

Provided were 8.87 mg (0.050 millimole) of palladium chloride, 2.50 g (12.5 millimoles) of cupric acetate monohydrate and 3.82 g (15.6 millimoles) of manganese(II) acetate tetrahydrate. After adding a small amount of methanol to the above mixture, 26.04 g (250.0 millimoles) of styrene was added. The resultant mixture was then added with 6.0 ml of a liquid prepared by causing methanol to absorb hydrogen chloride gas, the concentration of which liquid had been measured to be 1.07N immediately before its addition, so that the amount of hydrogen chloride in the reaction mixture reached 6.4 millimoles. More methanol was added to make the total volume be 125 ml.

The concentration o copper atoms per liter of the liquid reaction mixture was 0.10 gram atom, while the gram atom ratio of all chlorine atoms to all the copper atoms was 0.52. By using a reactor similar to that used in Example 26, a reaction was carried out in exactly the same manner as in Example 26 except that the total pressure was changed to 35 kg/cm$^2$G and a mixed gas containing carbon monoxide, oxygen and nitrogen at a partial pressure ratio of 9.9:5.1:85.0.

The conversion of styrene was 93.7%, while the selectivity toward methyl cinnamate and its yield were 89.1% and 83.5% respectively. The turnover number of palladium was 4180.

EXAMPLE 45

In the same manner as in Example 44, the same raw materials were charged in the same amounts except that a solution, which had been formed by causing methanol to absorb hydrogen chloride gas (concentration: 1.11N), was added in an amount of 6.0 ml, so that the amount of hydrogen chloride reached 6.7 millimoles. The concentration of copper atoms per liter of the liquid reaction mixture remained unchanged at 0.10 gram atom. The gram atom ratio of all chlorine atoms to all the copper atoms was 0.54. By using a reactor similar to that used in Example 26, a reaction was carried out in exactly the same manner as in Example 26 except that the total pressure was changed to 35 kg/cm$^2$G and a mixed gas containing carbon monoxide, oxygen and nitrogen at a partial pressure ratio of 8.9:5.5:85.6 was employed.

The conversion of styrene was 94.2%, while the selectivity toward methyl cinnamate and its yield were 91.3% and 86.0% respectively. The turnover number of palladium was 4300.

EXAMPLE 46

In the same manner as in Example 44, the same raw materials were charged in the same amounts except that a solution, which had been formed by causing methanol to absorb hydrogen chloride gas (concentration: 1.07N), was added in an amount of 5.0 ml so that the amount of hydrogen chloride reached 5.4 millimoles.

The concentration of copper atoms per liter of the liquid reaction mixture remained unchanged at 0.10 gram atom. The gram atom ratio of all chlorine atoms to all the copper atoms was 0.44. By using a reactor similar to that used in Example 26, a reaction was carried out in exactly the same manner as in Example 26 except that the total pressure was changed to 20 kg/cm$^2$G and a mixed gas containing carbon monoxide, oxygen and nitrogen at a partial pressure ratio of 8.9:5. 5:85.6 was employed.

The conversion of styrene was 89.3%, while the selectivity toward methyl cinnamate and its yield were 90.5% and 80.8% respectively. The turnover number of palladium was 4040.

EXAMPLE 47

Placed in a glass-made cylindrical vessel were 28.4 mg (0.160 millimole) of palladium chloride, 7.61 g (38.1 millimoles) of cupric acetate monohydrate and 12.3 g (50.2 millimoles) of manganese(II) acetate tetrahydrate. After adding a small amount of methanol to the resultant mixture, 83.33 g (800 millimoles) of styrene was added further. The resultant mixture was further added with 15.0 ml of a solution formed by causing methanol to absorb hydrogen chloride gas, the concentration of which liquid had been measured to be 1.5N right before the addition, so that the amount of hydrogen chloride reached 22.5 millimoles. Methanol was added further to make the total volume be 400 ml. The concentration of copper atoms per liter of the liquid reaction mixture was 0.095 gram atom, while the gram atom ratio of chlorine atoms to the copper atoms was 0.60. The glass vessel was then inserted in a 1-liter autoclave reactor, which was fitted with a TEFLON-made stirring blades, a glass-protected temperature measurement tube, a TEFLON-made gas inlet tube and a reflux condenser.

A feed gas mixture composed of carbon monoxide, oxygen and nitrogen at a ratio of 8.8:5.4:85.8 (vol. %; analyzed by gas chromatography) was prepared in advance in a pressure resistant vessel. This feed gas mixture was then introduced into the reactor. While maintaining the total pressure at 10 atms and causing the feed gas mixture to flow through the reactor in such a way that its flow velocity was 4.2 liters per minute (under standard conditions) at the outlet of the reactor, the contents were reacted at 100° C. for 3 hours with vigorous stirring. In the reactor, the partial pressures of carbon monoxide and oxygen were 0.88 atm and 0.54 atm respectively. During the reaction, the outlet gas was discharged through the water-cooled reflux condenser, and accompanying low b.p. materials were recirculated to the reactor. After the reaction, the autoclave was cooled and its pressure was released. The liquid reaction mixture was taken out of the autoclave and was then analyzed by liquid chromatography. It was found that the liquid reaction mixture contained 54.4 millimoles of styrene, 666.4 millimoles of methyl cinnamate and 16.3 millimoles of byproduced dimethyl phenyl succinate. The conversion of styrene was 93.2%, the selectivity toward methyl cinnamate (i.e., its yield based on the consumed styrene) was 89.4%, and yield of methyl cinnamate (based on the charged styrene) was 83.3%. The turnover number of palladium was 4170. In spite of the use of carbon monoxide and oxygen in the low partial pressures, high catalytic activities and good reaction results were obtained.

are shown in Table 5, along with results of Example 48.

TABLE 5

|  | Comp. Ex. 6 | Ex. 49 | Ex. 48 | Comp. Ex. 7 | Ex. 50 | Ex. 51 | Ex. 52 | Ex. 53 |
| --- | --- | --- | --- | --- | --- | --- | --- | --- |
| $Cu(OAc)_2 \cdot H_2O$* (millimole) | 0.31 | 18.0 | 30.0 | 182.8 | 34.3 | 23.1 | 10.0 | 0 |
| $CuCl_2$ (millimole) | 0.10 | 6.0 | 10.0 | 61.1 | 5.8 | 16.2 | 29.8 | 40.0 |
| Cu concentration (gram atom/liter) | 0.001 | 0.060 | 0.10 | 0.61 | 0.10 | 0.10 | 0.10 | 0.10 |
| Cl/Cu ratio by gram atom | 0.49 | 0.50 | 0.50 | 0.50 | 0.29 | 0.82 | 1.50 | 2 |
| Reaction time (hrs.) | 3.5 | 3.5 | 3 | 3 | 3 | 3 | 3 | 3 |
| Conversion of styrene (%) | 6.0 | 82.7 | 93.3 | 82.1 | 86.4 | 93.5 | 91.6 | 85.8 |
| Methyl cinnamate |  |  |  |  |  |  |  |  |
| Selectivity (%) | 46.7 | 90.1 | 92.4 | 45.3 | 90.4 | 91.4 | 85.3 | 51.5 |
| Yield (%) | 2.8 | 74.5 | 86.2 | 37.2 | 78.1 | 85.4 | 78.1 | 44.2 |
| Turnover number (mole/gram atom) | 140 | 3730 | 4310 | 1860 | 3910 | 4270 | 3910 | 2210 |

*"OAc" stands for an acetate group.

EXAMPLE 48

Provided were 35.92 mg (0.160 millimole) of palladium acetate, 5.99 g (30.0 millimoles) of cupric acetate monohydrate, 1.34 g (10.0 millimoles) of cupric chloride and 12.3 g (50.2 millimoles) of manganese(II) acetate tetrahydrate, followed by an addition of a small amount of methanol. Then, 83.33 g (800 millimoles) of styrene was added, followed by a further addition of methanol to bring the total volume to 400 ml. The concentration of copper atoms per liter of the liquid reaction mixture was 0.10 gram atom, while the ratio of chlorine atoms to the copper atoms was 0.50. They were reacted in the same manner as in Example 47.

The partial pressures of carbon monoxide and oxygen did not change and were 0.88 atm and 0.54 atm respectively.

The conversion of styrene was 93.3%, while the selectivity toward methyl cinnamate was 92.4% and its yield was 86.2%. The turnover number of palladium was 4310.

EXAMPLES 49-53 & COMPARATIVE EXAMPLES 6 AND 7

The procedures of Example 48 were exactly followed except that the amounts of cupric acetate monohydrate and cupric chloride and the reaction time were changed as given in Table 5. The partial pressures of carbon monoxide and oxygen changed slightly due to differences in composition of mixed gases upon their preparation. The changes were within 0.80–0.90 atm for carbon monoxide and within 0.50–0.57 atm for oxygen. Results

EXAMPLE 54

The procedures of Example 48 were exactly followed except that a mixed gas containing carbon monoxide, oxygen and nitrogen at a ratio of 8.5:5.3:86.2 (vol. %) was used and the total reaction pressure was changed to 6 atms. The partial pressures of carbon monoxide and oxygen were 0.51 atm and 0.32 atm respectively. The conversion of styrene was 88.6%, while the selectivity toward methyl cinnamate was 90.7% and its yield was 80.4%. The turnover number was 4020.

EXAMPLE 55

The procedures of Example 48 were exactly followed except that 510 mg of 5% Pd/C (catalyst composed of 5 wt. % of palladium carried on activated carbon) was used in placed of palladium acetate and the reaction time was changed to 3.5 hours. Methyl cinnamate was obtained with a yield of 72.3%.

EXAMPLES 50-59 & COMPARATIVE EXAMPLE 8

Reactions were respectively carried out in exactly the same manner as in Example 48 except that the palladium compounds shown in Table 6 was used in an amount of 0.13 millimole and the types and amounts of the components of the catalyst were changed as shown in Table 6. The partial pressures of carbon monoxide and oxygen ranges from 0.8 to 0.9 atm and from 0.50 to 0.57 atm respectively. The concentration of copper atoms in each liquid reaction mixture was 0.1 gram atom per liter, while the gram atom ratio of chlorine atoms to the copper atoms was 0.5. Results are summarized in Table 6.

TABLE 6

|  | Ex. 56 | Ex. 57 | Ex. 58 | Ex. 59 | Comp. Ex. 8 |
| --- | --- | --- | --- | --- | --- |
| Palladium compound | $PdCl_2$ | $Pd(OAc)_2$ | $Pd(OAc)_2$ | $PdCl_2$ | $PdCl_2$ |
| Components (millimoles) |  |  |  |  |  |
| 2nd component of catalyst | $Cu(OAc)_2 \cdot H_2O$* 40.0 | $Cu(phcoo)_2 \cdot 2H_2O$** 40.3 | $Cu(acac)_2 \cdot H_2O$ 30.0 | $Cu(OAc)_2 \cdot H_2O$ 30.0 | $Cu(OAc)_2 \cdot H_2O$ 30.0 |
| Halogen compound | $VOCl_3$ 6.7 | $POCl_3$ 6.7 | $CuCl_2$ 10.1 | $CuCl_2$ 9.9 | $CuCl_2$ 10.1 |

TABLE 6-continued

|  | Ex. 56 | Ex. 57 | Ex. 58 | Ex. 59 | Comp. Ex. 8 |
|---|---|---|---|---|---|
| 3rd component of catalyst | Zn(OAc)$_2$.H$_2$O  47.4 | Mn(acac)$_2$.2H$_2$O***  48.6 | Mn(OAc)$_2$.4H$_2$O  48.0 | MnCO$_3$  48.0 | None |
| Yield of methyl cinnamate (%) | 71.6 | 70.3 | 67.2 | 65.1 | 44.6 |
| Turnover number (mole/gram atom) | 4410 | 4330 | 4140 | 4010 | 2740 |

*"OAc" stands for an acetate group.
**"phcoo" stands for a benzoate group.
***"acac" stands for an acetylacetonate group.

EXAMPLE 60

Placed in a glass-made cylindrical vessel were 11.23 mg (0.050 millimole) of palladium acetate, 2.50 g (12.5 millimoles) of cupric acetate monohydrate and 3.74 g (15.0 millimoles) of cobalt(II) acetate tetrahydrate. After adding a small amount of methanol to the resultant mixture, 26.04 g (250.0 millimoles) of styrene was added further. The resultant mixture was further added with 5.0 ml of a solution formed by causing methanol to absorb hydrogen chloride gas, the concentration of which solution had been measured to be 1.25N right before the addition, so that the amount of hydrogen chloride reached 6.3 millimoles. Methanol was added further to bring the total volume to 125 ml. The concentration of copper atoms per liter of the liquid reaction mixture was 0.10 gram atom, while the gram atom ratio of chlorine atoms to the copper atoms was 0.50. The glass vessel was then inserted in a 500-ml autoclave. The stirring blades of the autoclave were made of glass and its temperature measurement tube was also protected with glass. While maintaining the total pressure at 51 atms and causing a feed gas mixture, which was composed of carbon monoxide, oxygen and nitrogen at a ratio of 8.5:5.3:86.2, to flow through the reactor in such a way that its flow velocity was 1.2 liters per minute (under standard conditions) at the outlet of the reactor, the contents were reacted at 100° C. for 3 hours with stirring. In the reactor, the partial pressures of carbon monoxide and oxygen were 4.3 atms and 2.7 atms respectively. During the reaction, the outlet gas was discharged through the water-cooled reflux condenser.

After the reaction, the autoclave was cooled and its pressure was released. The liquid reaction mixture was taken out of the autoclave and was then analyzed by liquid chromatography. It was found that the liquid reaction mixture contained 16.7 millimoles of styrene, 214.8 millimoles of methyl cinnamate and 7.14 millimoles of dimethyl phenyl succinate. The conversion of styrene was 93.3%, the selectivity toward methyl cinnamate (i.e., its yield based on the consumed styrene) was 92.1% and the yield of methyl cinnamate (based on the charged styrene) was 85.9%. The number of moles of the cinnamate ester produced per gram atom of the principal catalyst component, i.e., palladium, namely, the turnover number was 4300.

EXAMPLE 61

Provided were 11.23 mg (0.050 millimole) of palladium acetate, 1.87 g (9.37 millimoles) of cupric acetate monohydrate, 0.419 g (3.12 millimoles) of cupric chloride and 3.74 g (15.0 millimoles) of cobalt(II) acetate tetrahydrate, followed by an addition of a small amount of methanol. Then, 26.04 g (250.0 millimoles) of styrene was added, followed by a further addition of methanol to bring the total volume to 125 ml. The concentration of copper atoms per liter of the liquid reaction mixture was 0.10 gram atom, while the ratio of chlorine atoms to all the copper atoms was 0.50. They were reacted in the same manner as in Example 60 except that the reaction time was changed to 3.5 hours. The conversion of styrene was 90.2%, while the selectivity toward methyl cinnamate was 91.5% and its yield was 82.5%. The turnover number of palladium was 4130.

EXAMPLE 62

The procedures of Example 61 were exactly followed except that the total pressure of the reaction was changed to 10 atms. The conversion of styrene was 86.4%, while the selectivity toward methyl cinnamate was 90.9% and its yield was 78.5%. The turnover number of palladium was 3930.

EXAMPLE 63

The procedures of Example 61 were exactly followed except that the total pressure of the reaction was changed to 6 atms. The conversion of styrene was 85.1%, while the selectivity toward methyl cinnamate was 90.0% and its yield was 76.6%. The turnover number of palladium was 3830.

COMPARATIVE EXAMPLE 9

Following the procedures of Example 61, the same raw materials were charged in the same amounts except that the amount of cupric chloride was changed to 8.00 g (59.5 millimoles) and cupric acetate monohydrate was not used. The concentration of copper atoms per liter of the liquid reaction mixture was 0.48 gram atom, while the gram atom ratio of chlorine atoms to the copper atoms was 2. They were reacted in exactly the same manner as in Example 61 except that the total reaction pressure was changed to 10 atms. The conversion of styrene was 64.2%, while the selectivity toward methyl cinnamate was 5.7% and its yield was 3.7%. The turnover number of palladium was 190.

EXAMPLE 64

The procedures of Example 61 were exactly followed except that 170 mg of 5% Pd/C (catalyst composed of 5 wt. % of palladium carried on activated carbon) was used in place of palladium acetate. The conversion of styrene was 84.4%, while the selectivity toward methyl cinnamate was 77.3% and its yield was 65.2%.

EXAMPLES 65–68

The procedures of Example 61 were exactly followed except that the palladium compounds shown in Table 7 were each used in an amount of 0.04 millimole and the type and amount of the other components of the catalyst were changed as shown in Table 7. Results are shown in Table 7.

TABLE 7

|  | Ex. 65 | Ex. 66 | Ex. 67 | Ex. 68 |
|---|---|---|---|---|
| Palladium compound | PdCl$_2$ | Pd(OAc)$_2$ | PdCl$_2$ | PdCl$_2$ |
| Components (millimoles) |  |  |  |  |
| 2nd component of catalyst | Cu(OAc)$_2$.H$_2$O* | Cu(OAc)$_2$.H$_2$O | Cu(PhCOO)$_2$.2H$_2$O** | Cu(OAc)$_2$.H$_2$O |
|  | 12.5 | 15.0 | 12.5 | 13.0 |
| Halogen compound | FeCl$_3$ | VOCl$_3$ | Cl$_2$ | POCl$_3$ |
|  | 2.0 | 2.0 | 3.0 | 2.1 |
| 3rd component of catalyst | TiO(acac)$_2$*** | VO(acac)$_2$ | Co(OAc)$_2$.4H$_2$O | Ni(OAc)$_2$ |
|  | 15.6 | 10.0 | 15.0 | 15.0 |
| Yield of methyl cinnamate (%) | 68.3 | 72.3 | 78.8 | 75.4 |
| Turnover number (mole/gram atom) | 4270 | 4520 | 4930 | 4710 |

*"OAc" stands for an acetate group.
**"PhCOO" stands for a benzoate group.
***"acac" stands for an acetylacetonate group.

EXAMPLE 69

Placed in a glass-made cylindrical vessel were 4.5 mg (0.025 millimole) of palladium chloride, 1.87 g (9.37 millimoles) of cupric acetate monohydrate, 0.419 g (3.12 millimoles) of cupric chloride and 3.82 g (15.6 millimoles) of manganese(II) acetate tetrahydrate. After adding 26.04 g (250.0 millimoles) of styrene, methanol was added further to bring the total volume to 125 ml. The concentrations of copper atoms and chlorine atoms per liter of the liquid reaction mixture were 0.100 gram atom and 0.050 gram atom respectively. The glass vessel was then inserted in a 500-ml autoclave. The stirring blades of the autoclave were made of glass and its temperature measurement tube was also protected with glass. While maintaining the total pressure at 10 atms and causing a feed gas mixture, which was composed of carbon monoxide, oxygen and carbon dioxide at a ratio of 8.3:5.4:86.3, to flow through the autoclave in such a way that its flow velocity was 1.2 liters per minute (under standard conditions) at the outlet of the autoclave, the contents were reacted at 100° C. for 3 hours with stirring. During the reaction, the outlet gas was discharged through a water-cooled reflux condenser. After the reaction, the liquid reaction mixture was cooled and was then taken out of the autoclave. It was then analyzed by high-speed liquid chromatography. It was found that the liquid reaction mixture contained 20.0 millimoles of styrene, 210.8 millimoles of methyl cinnamate and 5.1 millimoles of dimethyl phenyl succinate. The conversion of styrene was 92.0%, the selectivity toward methyl cinnamate (i.e., its yield based on the consumed styrene) was 91.6% and the yield of methyl cinnamate (based on the charged styrene) was 84.3%. The number of moles of the cinnamate ester produced per gram atom of the first component of the catalyst, i.e., palladium, namely, the turnover number was 8430.

EXAMPLE 70

The procedures of Example 69 were exactly followed except that the mixed gas was changed to a mixed gas containing carbon monoxide, oxygen and nitrogen at a partial pressure ratio of 8.3:5.4:86.3 and containing no carbon dioxide. The conversion of styrene was 67.1%, while the selectivity toward methyl cinnamate was 93.4% and its yield was 62.7%. The turnover number of palladium was 6270. An analysis of a portion of the spent gas indicated the presence of carbon dioxide. This in turn indicates the formation of carbon dioxide by a side reaction.

EXAMPLES 71–73

The procedures of Example 69 were exactly followed except that the mixed gases shown in Table 8 were respectively employed. Results are shown in Table 8, along with results of Examples 69 and 70.

TABLE 8

|  | Mixed gas (proportions in partial pressure %) | | | | Conversion of styrene (%) | Methyl cinnamate | | Turnover number (mole/gram atom) |
|---|---|---|---|---|---|---|---|---|
|  | Carbon monoxide | oxygen | Carbon dioxide | Nitrogen |  | Selectivity (%) | Yield (%) |  |
| Ex. 70 | 8.3 | 5.4 | 0 | 86.3 | 67.1 | 93.4 | 62.7 | 6270 |
| Ex. 71 | 8.4 | 5.3 | 5.3 | 81.0 | 68.2 | 91.5 | 62.4 | 6240 |
| Ex. 72 | 8.5 | 5.6 | 20.5 | 65.4 | 87.2 | 92.0 | 80.2 | 8020 |
| Ex. 73 | 8.3 | 5.5 | 43.7 | 42.5 | 90.4 | 91.7 | 82.9 | 8290 |
| Ex. 69 | 8.3 | 5.4 | 86.3 | 0 | 92.0 | 91.6 | 84.3 | 8430 |

EXAMPLE 74

The procedures of Example 69 were exactly repeated except that the amount of cupric acetate monohydrate was changed to 2.50 g (12.5 millimoles) and in place of cupric chloride, 5.0 ml of a methanol solution of hydrogen chloride (concentration: 1.25 N) was used to achieve a hydrogen chloride of 6.25 millimoles. The concentrations of copper atoms and chlorine atoms were respectively 0.100 and 0.050 gram atom, both, per liter of the liquid reaction mixture. They were reacted in the same manner as in Example 69. The conversion of styrene was 90.5%, while the selectivity toward methyl cinnamate was 91.1% and its yield was 82.4%. The turnover number of palladium was 8240.

EXAMPLE 75

A reaction was carried out in exactly the same manner as in Example 74 except that the mixed gas was changed to a mixed gas containing carbon monoxide, oxygen and nitrogen at a partial pressure ratio of 8.3:5.4:86.3 and containing no carbon dioxide. The conversion of styrene was 68.8%, while the selectivity toward methyl cinnamate was 94.5% and its yield was 65.0%. The turnover number of palladium was 6500.

EXAMPLE 76

A reaction was carried out in exactly the same manner as in Example 74 except that the total reaction pressure was changed to 6 atms. The conversion of styrene was 87.2%, while the selectivity toward methyl cinnamate was 90.3% and its yield was 78.7%. The turnover number of palladium was 7870.

EXAMPLE 77

Added were 170 mg of 5% Pd/C (catalyst composed of 5 wt. % of palladium carried on activated carbon), 380 mg (2.2 millimoles) of vanadium oxytrichloride, 2.50 g (12.5 millimoles) of cupric acetate monohydrate and 3.82 g (15.6 millimoles) of manganese(II) acetate tetrahydrate. The resultant mixture was further added with 26.04 g (250 millimoles) of styrene, followed by an addition of methanol to bring the total volume to 125 ml. They were reacted in the same manner as in Example 69 except that the reaction time was changed to 3.5 hours. The conversion of styrene was 88.3%, while the selectivity toward methyl cinnamate was 91.1% and its yield was 80.4%.

EXAMPLE 78

A reaction was carried out in exactly the same manner as in Example 69 except that 5.6 mg (0.025 millimole) of palladium acetate and 3.74 g (15.0 millimoles) of cobalt(II) acetate tetrahydrate were used respectively in lieu of palladium chloride and manganese(II) acetate tetrahydrate, and the reaction time was changed to 3.5 hours. The conversion of styrene was 84.8%, while the selectivity toward methyl cinnamate was 91.3% and its yield was 77.4%. The turnover number of palladium was 7740.

EXAMPLE 79

A reaction was carried out in exactly the same manner as in Example 69 except that 9.0 mg (0.040 millimole) of palladium acetate and 697 mg (3.12 millimoles) of cupric bromide were used respectively in lieu of palladium chloride and cupric chloride, and a mixed gas containing carbon monoxide, oxygen and carbon dioxide at a partial pressure ratio of 8.7:5.7:85.6 was used. The conversion of styrene was 90.7%, while the selectivity toward methyl cinnamate was 93.0% and its yield was 84.3%. The turnover number of palladium was 5270.

EXAMPLE 80

A reaction was carried out in exactly the same manner as in Example 79 except that the mixed gas was changed to a mixed gas containing carbon monoxide, oxygen and nitrogen at a partial pressure ratio of 8.5:5.3:86.2 and containing no carbon dioxide. The conversion of styrene was 73.0%, while the selectivity toward methyl cinnamate was 69.5% and its yield was 50.7%. The turnover number of palladium was 3170.

EXAMPLES 81-92 & COMPARATIVE EXAMPLES 10 and 11

Reactions were conducted in exactly the same manner as in Example 69 except that the types and amounts of the catalyst components and reaction conditions were respectively changed as shown in Table 9. The partial pressure ratio of component gases in the mixed gas varied slightly whenever it was prepared. The degree of variations was within the range of 8.0–9.0:5-.0–6.0:85–87 as carbon monoxide:oxygen:carbon dioxide. Results are shown in Table 9, along with results of Example 79. In each of the Examples and Comparative Examples, better results were obtained compared with use of a mixed gas which was free of carbon dioxide.

TABLE 9

| | Components (millimoles) | | | | Reaction time (hrs.) | Total reaction pressure (atm.) | Yield of methyl cinnamate (%) | Turnover number (mole/gram atom) |
|---|---|---|---|---|---|---|---|---|
| | Palladium compound | 2nd component of catalyst | Halogen compound | 3rd component of catalyst | | | | |
| Ex. 79 | Pd(OAc)$_2$* 0.040 | Cu(OAc)$_2$.H$_2$O 9.4 | CuBr$_2$ 3.1 | Mn(OAc)$_2$.4H$_2$O 15.2 | 3 | 10 | 84.3 | 5270 |
| Ex. 81 | Pd(OAc)$_2$ 0.040 | Cu(PhCOO)$_2$.2H$_2$O** 12.5 | POCl$_3$ 2.1 | Mn(acac)$_2$.2H$_2$O*** 15.2 | 3 | 10 | 78.9 | 4930 |
| Ex. 82 | PdCl$_2$ 0.025 | Cu(OAc)$_2$.H$_2$O 9.4 | CuCl$_2$ 3.1 | Mn(CO$_3$)$_2$ 15.6 | 3 | 10 | 70.2 | 7020 |
| Ex. 83 | Pd(OAc)$_2$ 0.040 | Cu(acac)$_2$.H$_2$O 9.4 | CuCl$_2$ 3.1 | Mn(OAc)$_2$.4H$_2$O 15.0 | 3 | 10 | 77.5 | 4840 |
| Ex. 84 | PdCl$_2$ 0.040 | CuCO$_3$.Cu(OH)$_2$.H$_2$O 7.8 | CuCl$_2$ 3.1 | Mn(OAc)$_2$.4H$_2$O 15.6 | 3.5 | 51 | 63.5 | 3970 |
| Ex. 85 | PdCl$_2$ 0.040 | Cu(OAc)$_2$.H$_2$O 12.5 | VOCl$_3$ 2.1 | Zn(OAc)$_2$.2H$_2$O 15.1 | 3 | 10 | 84.0 | 5250 |
| Ex. 86 | PdCl$_2$ 0.040 | Cu(OAc)$_2$.H$_2$O 15.0 | VOCl$_3$ 2.0 | VO(acac)$_2$ 10.0 | 3.5 | 51 | 83.2 | 5200 |
| Ex. 87 | PdCl$_2$ 0.040 | Cu(OAc)$_2$.H$_2$O 12.5 | FeCl$_3$ 2.0 | TiO(acac)$_2$ 15.6 | 3.5 | 51 | 75.6 | 4730 |
| Ex. 88 | PdCl$_2$ 0.040 | Cu(OAc)$_2$.H$_2$O 12.5 | POCl$_3$ 2.1 | Ni(OAc)$_2$ 15.6 | 3.5 | 51 | 82.4 | 5150 |
| Ex. 89 | Pd(OAc)$_2$ 0.025 | Cu(OAc)$_2$.H$_2$O 12.5 | Cl$_2$ 3.2 | Mn(OAc)$_2$.4H$_2$O 15.6 | 3 | 10 | 76.8 | 7680 |
| Ex. 90 | PdCl$_2$ 0.040 | Cu(OAc)$_2$.H$_2$O 12.5 | SnCl$_4$ 1.6 | Mn(OAc)$_2$.4H$_2$O 15.6 | 3 | 10 | 79.8 | 4990 |
| Ex. 91 | PdCl$_2$ 0.040 | Cu(OAc)$_2$.H$_2$O 12.5 | BiCl$_3$ 2.1 | Mn(OAc)$_2$.4H$_2$O 15.6 | 3 | 10 | 70.6 | 4410 |
| Ex. 92 | PdCl$_2$ 0.040 | Cu(OAc)$_2$.H$_2$O 9.4 | CrCl$_3$ 2.1 | Mn(OAc)$_2$.4H$_2$O 15.6 | 3 | 10 | 86.9 | 5430 |
| Comp. Ex. 10 | PdCl$_2$ 0.050 | Cu(OAc)$_2$.H$_2$O 9.4 | CuCl$_2$ 3.1 | triethylamine 25.0 | 3 | 10 | 0.3 | 15 |
| Comp. | PdCl$_2$ | Cu(OAc)$_2$.H$_2$O | CuCl$_2$ | KOAc | 3 | 10 | 44.5 | 2230 |

TABLE 9-continued

| | Components (millimoles) | | | | Reaction time (hrs.) | Total reaction pressure (atm.) | Yield of methyl cinnamate (%) | Turnover number (mole/gram atom) |
|---|---|---|---|---|---|---|---|---|
| | Palladium compound | 2nd component of catalyst | Halogen compound | 3rd component of catalyst | | | | |
| Ex. 11 | 0.050 | 9.4 | 3.1 | 15.6 | | | | |

\*"OAc" stands for an acetate group.
\*\*"PhCOO" stands for a benzoate group.
\*\*\*"acac" stands for an acetylacetonate group.

COMPARATIVE EXAMPLE 12

The procedures of Example 69 were exactly followed except that the amounts of cupric acetate monohydrate and cupric chloride were changed respectively to 29.9 mg (0.15 millimole) and 13.4 mg (0.10 millimoles). The concentrations of copper atoms and chlorine atoms were the same, namely, 0.002 gram atom per liter of the liquid reaction mixture. They were reacted in the same manner as in Example 69. The conversion of styrene was 3.2%, while the yield of methyl cinnamate was less than 0.1%.

COMPARATIVE EXAMPLE 13

The procedures of Example 69 were exactly repeated except that the amounts of cupric acetate monohydrate and cupric chloride were changed respectively to 1.20 g (6.01 millimole) and 8.07 g (60.0 millimoles). The concentrations of copper atoms and chlorine atoms were 0.528 gram atom and 0.960 gram atom respectively, both per liter of the liquid reaction mixture. They were reacted in the same manner as in Example 69. The conversion of styrene was 53.2%, while the selectivity toward methyl cinnamate was 8.4% and its yield was 4.5%.

EXAMPLE 93

A glass-made cylindrical vessel was charged in the same manner as in Example 69. The procedures of Example 69 were repeated except that the total reaction pressure was changed to 51 atms, a mixed gas containing carbon monoxide, oxygen and carbon dioxide at a partial pressure ratio of 8.6:5.4:86.0 was fed in such a way that the spent gas had a flow velocity of 1.2 liters per minute (under standard conditions) at the outlet of a reflux condenser, and the spend gas was caused to flow through a dry ice trap and was then stored in a pressure resistant vessel (about 10 l) which had in advance been purged once with the above feed gas mixture. The conversion of styrene was 94.6%, while the selectivity toward methyl cinnamate was 92.2% and its yield was 87.2%. The gas stored in the pressure resistant vessel was analyzed, and carbon monoxide and oxygen were added to the gas in order to adjust is partial pressure ratio of carbon monoxide:oxygen:carbon dioxide to 8.7:5.5:84.6. The gas contained a small amount (partial pressure ratio: 1.2%) of nitrogen mingled therein. The pressure of the final gas in the pressure resistant vessel was about 25 atms. In a glass-made cylindrical vessel for a 200-ml autoclave, were placed 1.8 mg (0.010 millimole) of palladium chloride, 748 mg (3.75 millimoles) of cupric acetate monohydrate, 168 mg (1.25 millimoles) of cupric chloride and 1.53 g (6.24 millimoles) of manganese(II) acetate tetrahydrate. Thereafter, 10.42 g (100.0 millimoles) styrene was added. The total volume was then brought to 50 ml with methanol. That glass-made vessel was inserted in a 200-ml autoclave. In the same manner as in Example 69, the contents were reacted while maintaining the total pressure at 10 atms and causing the above-prepared mixed gas to flow in such a way that the flow velocity of the spent gas was 500 ml/min (under standard conditions) at the outlet. The conversion of styrene was 90.3%, while the selectivity toward methyl cinnamate was 93.1% and its yield was 84.1%.

What is claimed is:

1. A process for preparing a cinnamate ester by the reaction of carbon monoxide, oxygen, and its corresponding styrene compound and alcohol, which comprises conducting the reaction in the presence of a catalyst containing, as essential components,
    (a) a platinum group metal or a compound thereof;
    (b) a copper or iron compound; and
    (c) a compound of at least one metal selected from Groups 4A, 5A, 7A, 8A(the iron group only), 1B(exclusive of copper) and 2B of the periodic table.

2. A process as claimed in claim 1, wherein carbon dioxide is caused to exist in the reaction system.

3. A process as claimed in claim 1, wherein the component (a) is metallic palladium or a compound thereof.

4. A process as claimed in claim 2, wherein the component (a) is metallic palladium or a compound thereof.

5. A process as claimed in claim 1, wherein the component (b) is a copper compound.

6. A process as claimed in claim 2, wherein the component (b) is a copper compound.

7. A process as claimed in claim 1, wherein the component (c) is a compound of at least one metal selected from Groups 5A, 7A, 8A(the iron group only) and 2B.

8. A process as claimed in claim 2, wherein the component (c) is a compound of at least one metal selected from Groups 5A, 7A, 8A(the iron group only) and 2B.

9. A process as claimed in claim 5, wherein the copper compound is the copper salt of an organic acid or a complex compound of copper.

10. A process as claimed in claim 6, wherein the copper compound is the copper salt of an organic acid or a complex compound of copper.

11. A process as claimed in claim 7, wherein the component (c) consists of vanadium, manganese, cobalt, nickel and/or zinc compounds.

12. A process as claimed in claim 8, wherein the component (c) consists of vanadium, manganese, cobalt, nickel and/or zinc compounds.

13. A process as claimed in claim 1, wherein the catalyst contains, as an additional component (d), a halogen compound.

14. A process as claimed in claim 13, wherein carbon dioxide is caused to exist in the reaction system.

15. A process as claimed in claim 13, wherein the component (a) is metallic palladium or a compound thereof.

16. A process as claimed in claim 14, wherein the component (a) is metallic palladium or a compound thereof.

17. A process as claimed in claim 13, wherein the component (b) is a copper compound.

18. A process as claimed in claim 14, wherein the component (b) is a copper compound.

19. A process as claimed in claim 13, wherein the component (c) is a compound of at least one metal selected from Groups 5A, 7A, 8A(the iron group only) and 2B.

20. A process as claimed in claim 14, wherein the component (c) is a compound of at least one metal selected from Groups 5A, 7A, 8A(the iron group only) and 2B.

21. A process as claimed in claim 17, wherein the copper compound is the copper salt of an organic acid or a complex compound of copper.

22. A process as claimed in claim 18, wherein the copper compound is the copper salt of an organic acid or a complex compound of copper.

23. A process as claimed in claim 19, wherein the component (c) consists of vanadium, manganese, cobalt, nickel and/or zinc compounds.

24. A process as claimed in claim 20, wherein the component (c) consists of vanadium, manganese, cobalt, nickel and/or zinc compounds.

25. A process as claimed in claim 17, wherein the concentration of copper atoms in the liquid reaction mixture is controlled at 0.004–0.4 gram atom per liter and the atomic ratio of halogen atoms to copper atoms is maintained smaller than 2.

26. A process as claimed in claim 18, wherein the concentration of copper atoms in the liquid reaction mixture is controlled at 0.004–0.4 gram atom per liter and the atomic ratio of halogen atoms to copper atoms is maintained smaller than 2.

27. A process as claimed in claim 13, wherein the halogen compound is a chlorine compound.

28. A process as claimed in claim 14, wherein carbon dioxide contained in a residual gas or spent gas after the reaction is used for the entire or partial portion of carbon dioxide to be caused to exist in the reaction system.

* * * * *